United States Patent [19]

Vogelstein

[11] Patent Number: 5,009,593
[45] Date of Patent: Apr. 23, 1991

[54] METHOD AND APPARATUS FOR SECURING A DENTAL RESTORATION

[75] Inventor: Henry J. Vogelstein, New York, N.Y.

[73] Assignee: Coltene/Whaledent, Inc., New York, N.Y.

[21] Appl. No.: 475,649

[22] Filed: Feb. 5, 1990

[51] Int. Cl.$^5$ ............................................. A61C 5/08
[52] U.S. Cl. .................................. 433/221; 433/228.1
[58] Field of Search ............... 433/220, 221, 225, 215, 433/216, 81, 224, 102

[56] References Cited

U.S. PATENT DOCUMENTS

| | | | |
|---|---|---|---|
| 4,645,457 | 2/1987 | Goldman et al. | 433/220 |
| 4,659,751 | 4/1987 | Bowen | 433/228.1 |
| 4,758,163 | 7/1988 | Goldman | 433/229 |
| 4,801,528 | 1/1989 | Bennett | 433/220 |
| 4,850,872 | 7/1989 | Goldman et al. | 433/215 |
| 4,936,775 | 6/1990 | Bennett | 433/220 |

Primary Examiner—Cary E. Stone
Attorney, Agent, or Firm—Helfgott & Karas

[57] ABSTRACT

A method for restoring a tooth by endodontically preparing the tooth to accept a dental post. Polyacrylic acid solution is supplied to the prepared area afterwhich it is rinsed out and the area dried. A drying agent has been applied to the prepared area and, likewise, the area is dried out. The dental post is then secured in place through the use of a cement. Preferably, the cement is a filled resin cement with the filler material being approximately 15%-30% of the cement. The drying agent is preferably an ethyl-methyl ketone. The invention also includes a kit containing the materials for implementing the method.

30 Claims, 2 Drawing Sheets

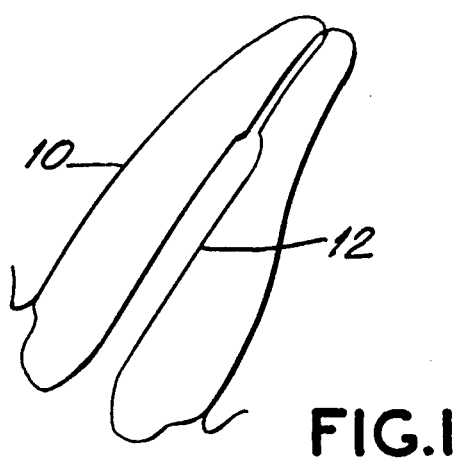
FIG.1
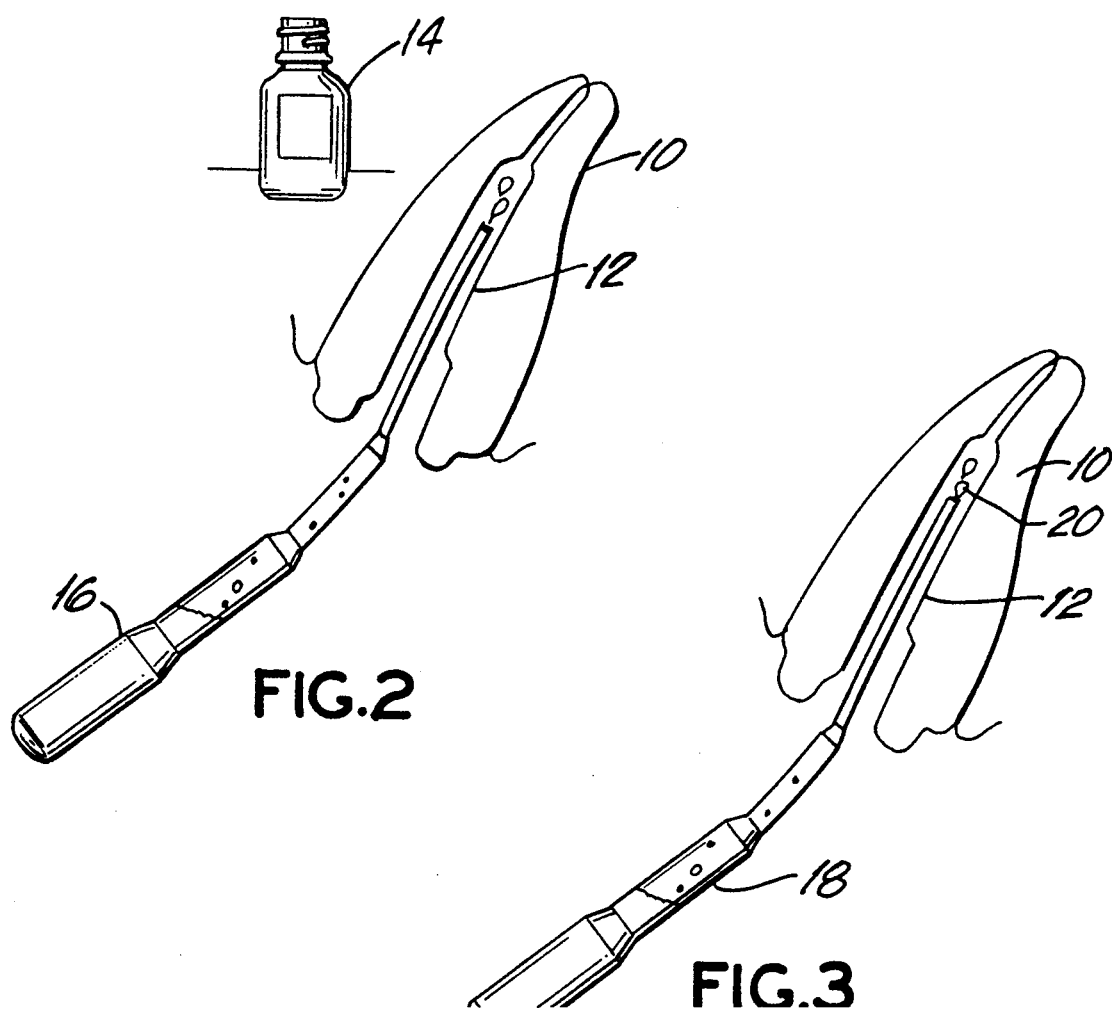
FIG.2
FIG.3

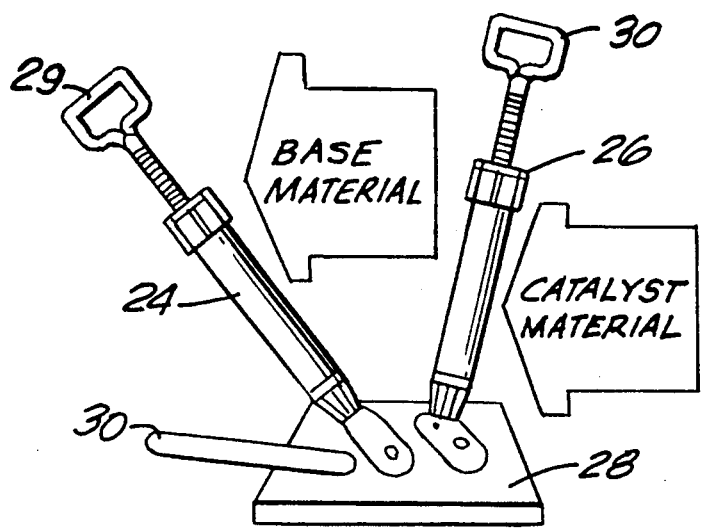
FIG. 4
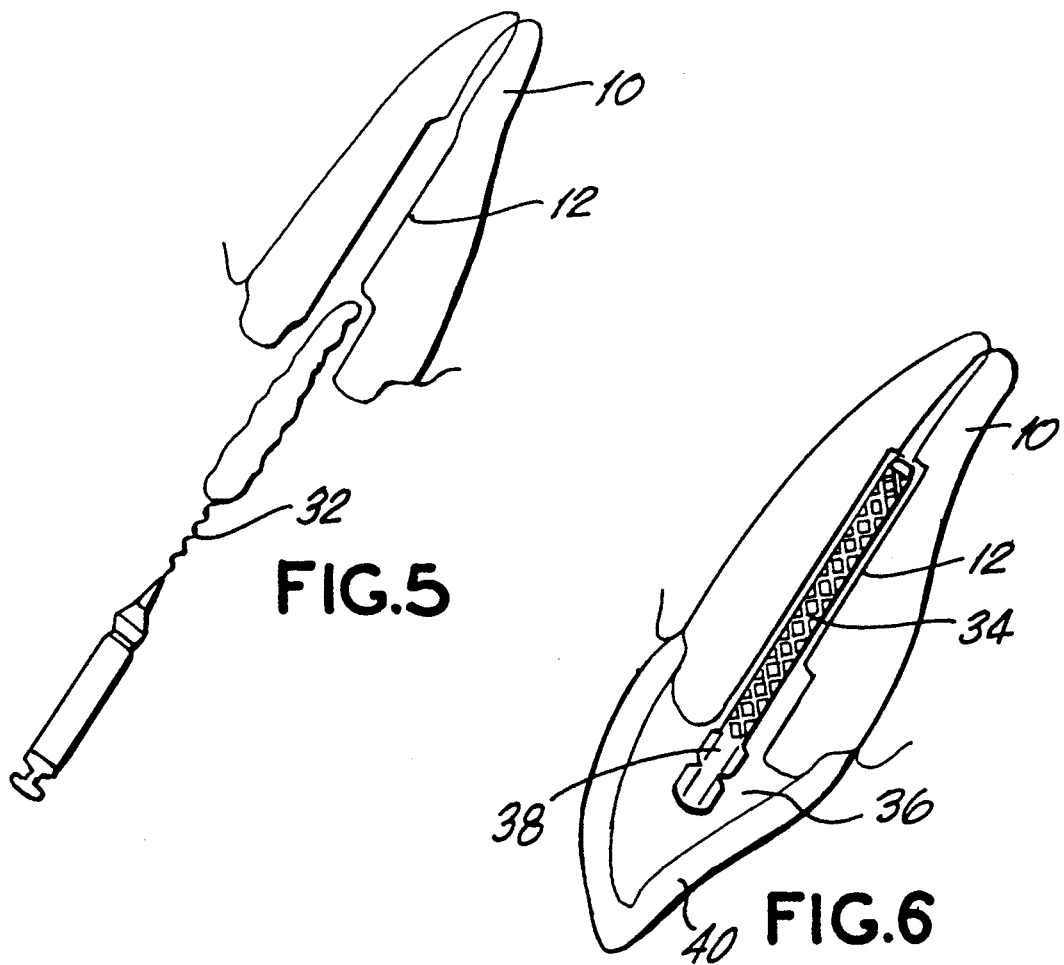
FIG. 5
FIG. 6

METHOD AND APPARATUS FOR SECURING A DENTAL RESTORATION

BACKGROUND OF THE INVENTION

This invention relates to dental restorations, and more particularly, to a method and apparatus for securing a dental post within a prepared endodontically treated tooth in connection with a coronal replacement using a post and cement techniques.

One of the most commonly used dental restorations is the formation of a crown to replace a missing coronal tooth structure. Such techniques generally involve formation of a bore, typically along the apical canal and the securement of a post within the bore. A core is built up onto the post head protruding from the bore, and an artificial crown is then secured in place on the core.

Various types of dental posts have been utilized for maintaining the superstructure in place. One type of post, generally referred to as active post, uses external threads for threading the post into the tooth understructure. While these active posts provide good retention, they generally increase the amount of stress in the tooth understructure and may cause cracking of the tooth. Additionally, even these active posts use cement in addition to the screw threads to retain the post in place.

Other types of posts are referred to as passive posts. While these include grooves to aid in the retention, they rely upon cement to secure the post in place. These passive posts generally do not provide the stress of the active posts. However, in order to provide good retention, adequate cementing techniques are required.

Numerous cements have been known to provide good to excellent results. Some of the more common cements that have been used include those of zinc phosphate, glass-ionomer cement, polycarboxylate, zinc oxide, and resins. One of the most common forms of the resin cement is a Bis-GMA resin. In addition, acrylic base cements have also been utilized such as a methacrylate.

In addition to relying upon the cement alone, additional techniques have been introduced to increase the retention with the available cements. A most common approach is to roughen the post space with a threader, or the like. Occasionally, this technique is referred to as providing a "corrugated" canal to enhance the cementation process.

U.S. Pat. No. 4,645,457 issued to Goldman and Nathanson, provides yet a further method for enhancing the cementing technique. This patent teaches that after forming the bore, there are dentinal tubules existing within the tooth understructure. However, there exists a sludge or smear layer that covers a portion of the bore or canal walls. This appears as an amorphous layer on the canal wall that obstructs the dentinal tubules. This patent, accordingly, teaches the use of a specific sequence of steps in order to prepare the tooth for a coronal replacement and achieve enhanced retention. The patent teaches a first step of flushing the prepared area with a chelating agent selected from the group consisting of citric acid and ethylenediaminetetraacetic acid (EDTA). This material serves to remove the debris and the smear layer. Thereafter, in a second step, which must follow the previous step, a solvent selected from the group consisting of sodium hypochlorite (NaOCl), surface active agents, and emulsifiers are used. This serves to open up the tubules. Thereafter, a suitable luting agent is utilized to secure the post in place.

Subsequent to the above identified patent, a continuation of this patent issued as U.S. Pat. No. 4,758,163 which covered a kit for applying these materials. A subsequent U.S. Pat. No. 4,850,872 issued also on this technique applying the technique to other types of restorations, including placing filler material in a tooth having a caries cavity.

The above mentioned technique covered by the patent, has been licensed to Roydent Company and the preferred material utilized in the commercially available product includes the use of EDTA and NaOCl. The cement that is used is an unfilled Bis-GMA resin. The cement has also been referred to as the Boston Post cement.

While various tests have been conducted to determine which of the various cements provide the best retention, in a study by Anthony H.L. Tjan, et al., in the Journal of Prosthetic Dentistry, September 1987, Volume 58, #3 in an article entitled "Effects of Various Cementation Methods on the Retention of Prefabricated Posts", it would appear that the best type of retention can be obtained by roughening the post hole prior to utilization of a cement. Furthermore, the type of cement that this article found to be most effective was a resin cement which was used after roughening the post holes using a tap. With such technique, the retention shown was an average of about 120 lbs. Using the technique described in the aforementioned patent, namely, providing initially a rinse of EDTA followed by an irrigation of NaOCl, and thereafter, use of the resin, the retention was an average of only approximately 55 lbs.

The type of resin that was used in this article was a highly filled resin which was selected because it has a lower polymerization shrinkage and higher mechanical strength than unfilled resin. Generally, the more filled the resin is, the lower the polymerization shrinkage. Accordingly, for this reason a high amount of filler was utilized in order to get a lower polymerization shrinkage.

The particular resin described in this article was a composite resin available from Sci-Pharm, Inc. in Duarte, Calif., available under the brand name of Support P/L.

While this Journal article pointed out that improved retention can be achieved through roughening the dental walls, such roughening can apply additional stress to the post canal, can weaken the wall, and adds additional time and complexity to the cementing process.

It would, accordingly, be beneficial if improved cementing techniques could be achieved whereby retention can be increased without the necessity of roughening or corrugating the canal walls.

SUMMARY OF THE INVENTION

Accordingly, it is object of the present invention to provide an improved cementing technique for restoring a tooth.

Another object of the present invention is to provide an improved method for retaining a dental prosthesis onto a prepared tooth providing increased retention.

Yet, another object of the present invention is to provide a method of retaining a post in a prepared canal which provides improvement without the need for corrugating the canal.

A further object of the present invention is to provide a kit for use in dental restorations and, specifically, in connection with securement of endodontic posts.

Briefly, in accordance with the present invention, there is provided a method for restoring a tooth including the steps of first preparing the tooth to accept the dental prosthesis. Thereafter, a polyacrylic acid solution is applied to the prepared area. The prepared area is then thoroughly rinsed until it is clear from the polyacrylic acid solution. Thereafter, a drying agent is applied to the prepared area. Following the drying of the area, the dental prosthesis is secured to the prepared area through the use of a dental cement.

In a preferred embodiment of the invention, the cement that is used is a filled resin cement, wherein the amount of filler is between 15% and 30%. Preferably prior to applying the drying agent, the polyacrylic acid is rinsed with water to completely remove the polyacrylic acid solution.

The drying agent can be any of a number of available drying agents, preferably the drying agent is an ethylmethyl ketone.

The particular method is specifically useful in connection with securement of a dental post in the formation of a crown to replace a missing coronal area of the dentition. Initially, the tooth is endodontically prepared including formation of a bore or canal in the tooth. The canal is sealed in accordance with the usual endodontic techniques for insertion of the post. Thereafter, the above method is utilized for securing the post in place. The core is then built up on the post head and thereafter, a suitable coronal restoration can be secured in place on the core.

The present invention also contemplates providing a kit including the materials required for implementing the above method. The kit would include the polyacrylic acid solution, together with the drying agent, and the necessary dental cement. Additional mechanical implements such as pipettes, and the like, can also be included within the kit encompassed with the present invention.

The aforementioned objects, features and advantages of the invention will, in part, be pointed out in particularity, and will, in part, become obvious from the following more detailed description of the invention, taken in conjunction with the accompanying drawing, which forms an integral part thereof.

BRIEF DESCRIPTION OF THE DRAWING

In the drawing:

FIG. 1 is a schematic view of a tooth prepared for receiving a dental prosthesis, and specifically, a dental post;

FIG. 2 shows a first step in applying the method, namely, application of a dental preparatory material, and specifically, polyacrylic acid;

FIG. 3 shows another step in the method, and specifically, the application of the drying agent;

FIG. 4 shows a further step, and specifically, the formation of the cement by combining a base material and a catalyst material;

FIG. 5 shows a further step in the method, and specifically, the application of the cement into the prepared canal, and FIG. 6 shows a final step wherein a post has been secured in the prepared canal and a core and final coronal restoration has been completed on the tooth understructure.

In the various figures of the drawing, likewise, its characters designate like parts.

DESCRIPTION OF THE INVENTION

Referring back to FIG. 1, there is shown a dental understructure 10 which has undergone endodontic therapy. The tooth is then prepared for restoration as if the pulp were intact. The preparation includes at least 1.5 mm of sound tooth structure apical to the core for a desired ferrule effect. If that amount of tooth structure is not available, it should be created by periodontal crown lengthening or forced eruption. As shown in FIG. 1, the apical portion is designated at about 4 mm with the sound tooth being of about 1.5 mm. The prepared canal is shown at 12. If necessary, a radiograph can be used to determine the suitable diameter and depth of the post space preparation.

The gutta-percha is removed to a desired depth with a Gates Glidden drill, Peeso reamer, or hot instrument. At least 4 mm of gutta-percha should be maintained to protect the apical seal. Again, radiographic verification can be used for this purpose.

As is well known in the art, if the canal has been obturated with a silver cone, it should be removed and the apex resealed with gutta-percha before preparation of the post space. The post space is then prepared in accordance with the type of post being utilized.

The present cementing procedure is shown in FIG. 2 wherein a bottle of the dental preparation material 14 contains the polyacrylic acid solution. A fresh clean pipette 16 is used to pick up the dental preparation material from the bottle 14. Enough material is used to fill the lower chamber of the pipette. The polyacrylic acid material is then applied into the prepared canal 12. Typically, the material is applied from the bottom of the sealed canal by back filling.

The dental preparation material, specifically, the polyacrylic acid solution, is syringed into the bottom of the canal with the pipette. The material is left there for a short period of time, typically, approximately 20 secs. Thereafter, the canal is rinsed with water until it is clear from the polyacrylic acid solution. The canal is then dried completely with endodontic absorbent points.

Refer now to FIG. 3, another pipette 18 is now utilized to apply a drying agent material 20 into the canal 12. The drying agent is again kept in the canal for a short period of time, typically, about 10 secs. The canal is then dried with endodontic absorbent points. Both pipettes can be discarded after their individual use.

Refer now to FIG. 4, wherein the cement is mixed. Typically, the cement comprises a first part generally referred to as the base material contained in a first dispensing syringe 24, and a second part, typically, the catalyst material provided in a second dispensing syringe 26. Generally, these are referred to typically as Parts A and B of the cement material. The two parts are placed in equal amount on a mixing pad 28. In the type of syringes 24, 26 the amount of material expressed from the syringes can be controlled by the amount of turning of the handles 29, 30. By rotating each equal amount, equal amount of materials will be expressed from the syringes 24, 26.

The Parts A and B are mixed well with a spatula 30, typically, for about 30 secs., or until a uniform color is obtained.

As shown in FIG. 5, a lentulo spiral 32 is then utilized to spin the cement material into the canal 12. The canal walls are completely covered. Likewise, the post 34, prior to placement, is also coated with cement. The post is then fully seated into the canal 12. The excess cement vents to the outside of the canal and then is removed. After the cement is set, a core 36 is built up onto the post head 38 and, thereafter, the suitable crown or other coronal restoration 40 is completed.

The dental preparation material is a polyacrylic acid solution. It has been found, that this solution should contain between 10% and 25% of polyacrylic acid. The molecular weight should be between 25,000 and 100,000. Generally, it has been found that the higher molecular weight, the greater the viscosity of the material.

The drying agent is an ethyl-methyl ketone. Such drying agents are available from various sources, such as the product Cavidry, available from Parkell, Farmingdale, N.Y. having acting ingredients of ethyl-methyl ketone and ethyl-acetate. Another such product is sold under the name Cavilax, by the Premier Dental Products Co., Morristown, Pa., and manufactured in Germany by ESPE GmbH and Co.

The type of cement that is being utilized is a Bis-GMA resin cement, having a small amount of filler, typically, between 15% and 30%. The filler can be any filler material such as mica, glass, or preferably silica. The particle size of the silica should be less than 1 micron. Such bis-GMA cement is virtually the same as that used in the Boston Post system, however, that cement is an unfilled resin while it has been preferably been found that by using a limiting amount of filler, the compressive strength is increased. Although use of only a small amount of filler provides a greater amount of polymerization shrinkage than would be if a larger amount of resin is utilized, however, an improvement in retention has been found with the limited amount of filled resin. Concerning the polymerization shrinkage, since the material is used in small quantities and thin layers, the shrinkage has not been found to be any problem. Furthermore, the shrinkage in any event would be less than that of the Boston Post cement which has been used quite successfully. The handling characteristics of the cement has been found to be very favorable, handling better than prior art cements.

In tests conducted with various available cements, it has been found that the present cement with the method described has provided far superior results, and in fact, has provided results comparable to that achieved with the use of a corrugated canal, yet, without the stress resulting from corrugations. The following is a summary of the test results. The values are given in Kgs required to unseat the post. In all instances, with the resin cements, the cement separated at the tooth cement interface.

|  | Mean Kg |  | Std. Dev. |
| --- | --- | --- | --- |
| Roydent without EDTA | 15.6 | ± | 5.46 |
| Durelon | 18.2 | ± | 4.04 |
| Roydent with EDTA | 26.0 | ± | 13.14 |
| Zinc Phosphate | 30.2 | ± | 7.55 |
| Present Method without PAA | 30.3 | ± | 10.33 |
| Present Method with PAA | 54.8 | ± | 16.88 |

In connection with the ratio of the Part A to Part B cement, the changes in these ratios only affect the working and setting time. More Part A, namely, more base material provides a faster set while more Part B provides a slower set. The mechanical properties remain virtually unchanged.

Although the specific reason for the unexpected and unusual improved results of the present method may depend upon a number of factors, it is believed that one of the key factors is the particular steps utilized. The polyacrylic acid provides the necessary cleaning of the debris in the canal, as well as removal of the smear layer. Subsequently, rinsing removes the polyacrylic acid along with the rest of the debris material. It is believed, however, in prior methods, when various chemicals were used to open the tubules, the chemicals remained in the tubules and therefore prevented adequate cement from filling the tubules. It is believed that through the use of the drying agents, the tubules are dried out from liquid, including the water rinse. As a result, the tubules are now completely open so that when the cement is utilized, it provides improved mechanical bonding by flowing into the open tubules to provide additional retention.

Furthermore, the use of the filled resin, with the filler material being used to only a small percentage, provides unusual improved retention better than heretofore found without fillers or even with highly filled resin.

While the aforementioned description was in connection with the cementing of an endodontic post, it is believed that the present cement and the method described will find use in other types of dental restorations where improved retention is required.

There has been disclosed heretofore the best embodiment of the invention presently contemplated. However, it is to be understood that various changes and modifications may be made thereto without the departing from the spirit of the invention.

I claim:

1. A method for restoring a tooth, comprising the steps of:
    (a) preparing the tooth to accept a dental prosthesis;
    (b) applying a polyacrylic acid solution to the prepared area;
    (c) rinsing the prepared area until the area is clear from the polyacrylic acid solution;
    (d) applying a drying agent to the prepared area; and
    (e) securing a dental prosthesis to the prepared area through the use of a dental cement.

2. The method of claim 1, wherein the dental cement is a two part cement including a base and a catalyst.

3. The method of claim 1, wherein the cement is a filled resin cement.

4. The method of claim 3, wherein said cement is a Bis-GMA cement.

5. The method of claim 3, wherein the filler material is selected from the group consisting of mica, glass, and silica.

6. The method of claim 1, wherein the cement includes between 15%-30% filler.

7. The method of claim 6, wherein said cement is an acrylic base cement.

8. The method of claim 1, wherein the filler has a particle size below 1 micron.

9. The method of claim 1, wherein the polyacrylic acid solution comprises between 10%-25% polyacrylic acid.

10. The method of claim 9, wherein the polyacrylic acid has a molecular weight of between 25,000 to 100,000.

11. The method of claim 1, wherein the drying agent is an ethyl-methyl ketone.

12. The method of claim 1, and further comprising the step of drying the prepared area both after the step of rinsing and after the step of applying a drying agent.

13. The method of claim 1, wherein said rinsing is achieved with water.

14. The method of claim 1, wherein said prosthesis is a dental crown secured by a dental post, and wherein said step of preparing includes formation of an apical bore in the tooth to receive the dental post, and wherein the dental post is seated in the bore with the dental cement.

15. A method of fabricating a dental restoration, comprising the steps of:
 (a) preparing the tooth including formation of an apical bore in the tooth;
 (b) applying a polyacrylic acid solution to the bore;
 (c) rinsing the bore until it is clear from the solution;
 (d) applying a drying agent to the bore;
 (e) cementing a post into the bore; and
 (f) forming a core and restoration on the post.

16. The method of claim 15, wherein cement used in said cementing step is a filled resin cement.

17. The method of claim 16, wherein the cement is a filled Bis-GMA cement.

18. The method of claim 16, wherein the filler material is selected from the group consisting of mica, glass, and silica.

19. The method of claim 15, wherein the drying agent is an ethyl-methyl ketone.

20. A kit for use in securing a dental prosthesis to a prepared tooth, comprising:
 polyacrylic acid solution for cleaning the prepared tooth area;
 a drying agent for application to the prepared area to completely dry out the prepared area; and
 a dental cement for securing a dental prosthesis to the prepared area.

21. A kit as in claim 20, wherein the cement is a filled resin cement.

22. The kit of claim 21, wherein the filler is between 15%-30% of the cement.

23. The kit of claim 22, wherein the filler has a particle size below 1 micron.

24. The kit of claim 21, wherein the filler is selected from the group consisting of mica, glass, and silica.

25. The kit as in claim 21, further comprising pipettes for applying the polyacrylic acid solution and for applying the drying agent.

26. The kit of claim 20, wherein the cement is a filled Bis-GMA cement.

27. The kit of claim 20, wherein the cement is a filled acrylic base cement.

28. The kit of claim 20, wherein the drying agent is an ethyl-methyl ketone.

29. The kit of claim 20, wherein the polyacrylic acid solution comprises between 10%-25% polyacrylic acid.

30. The kit as in claim 29, wherein the polyacrylic acid has a molecular weight of between 25,000-100,000.

* * * * *